United States Patent [19]

Sweeney

[11] Patent Number: 4,849,131
[45] Date of Patent: Jul. 18, 1989

[54] NONIONIC EMULSIFIER AND SUBSTITUTED SUCCINIC ANHYDRIDE COMPOSITIONS THEREWITH

[75] Inventor: William A. Sweeney, Larkspur, Calif.

[73] Assignee: Chevron Research Company, San Francisco, Calif.

[21] Appl. No.: 106,741

[22] Filed: Oct. 8, 1987

Related U.S. Application Data

[63] Continuation of Ser. No. 880,386, Jun. 30, 1986, abandoned, which is a continuation of Ser. No. 509,270, Jun. 29, 1983, abandoned.

[51] Int. Cl.$^4$ .................. B01F 17/00; B01F 17/36; B01J 13/00
[52] U.S. Cl. .................. 252/312; 162/158; 252/174.21; 252/351; 252/356; 252/DIG. 1
[58] Field of Search ........... 252/312, 351, 356, 174.21, 252/DIG. 1

[56] References Cited

U.S. PATENT DOCUMENTS

| | | | |
|---|---|---|---|
| 3,057,890 | 10/1962 | DeGroote | 560/198 X |
| 3,086,044 | 4/1963 | Kerschner et al. | 560/199 |
| 3,231,587 | 1/1966 | Rense | 560/190 X |
| 3,419,665 | 12/1968 | Lachampt et al. | 574/785 |
| 3,431,063 | 3/1969 | Fox | 252/351 X |
| 3,579,453 | 5/1971 | Dupre et al. | 252/174.19 |
| 3,968,310 | 7/1976 | Stowell | 428/411 |
| 4,256,605 | 3/1981 | Baker | 252/312 |
| 4,529,447 | 7/1985 | Okada et al. | 106/287.24 |

FOREIGN PATENT DOCUMENTS

| | | |
|---|---|---|
| 0074619 | 3/1983 | European Pat. Off. . |
| 0107199 | 5/1984 | European Pat. Off. . |
| 896376 | 5/1962 | United Kingdom . |
| 1087635 | 10/1967 | United Kingdom . |
| 1588067 | 4/1981 | United Kingdom . |

*Primary Examiner*—Richard D. Lovering
*Attorney, Agent, or Firm*—S. R. La Paglia; R. C. Gaffney; C. J. Caroli

[57] ABSTRACT

A nonionic emulsifier derived from mono-ester reaction products of substituted succinic anhydride. There is also disclosed a stable substituted succinic anhydride/nonionic emulsifier composition, a method for imparting water repellency to surfaces containing groups reactive to anhydrides, and a method for the sizing of paper using said composition.

17 Claims, No Drawings

NONIONIC EMULSIFIER AND SUBSTITUTED SUCCINIC ANHYDRIDE COMPOSITIONS THEREWITH

This is a continuation of application Ser. No. 880,386, filed June 30, 1986, now abandoned, which is a continuation of Ser. No. 509,270, filed June 29, 1983, now abandoned.

BACKGROUND OF THE INVENTION

This invention relates to a novel nonionic emulsifier. This invention also relates to an improved hydrocarbyl-substituted succinic anhydride/nonionic emulsifier composition. Another aspect of this invention relates to an improved method for imparting water repellency to surfaces containing groups reactive to anhydrides. A further aspect of this invention relates to an improved method for the sizing of paper and paperboard products.

It is well known in the art that hydrocarbyl-substituted succinic anhydrides are good for treating paper, fabric, or other surfaces to impart water repellency. As indicated in U.S. Pat. Nos. 3,102,064, 3,821,069, 3,968,005, and 4,040,900 (Re. No. 29,960), these compositions are particularly useful for sizing paper.

It is also known that these succinic anhydrides are best applied for such purposes in a highly dispersed form, such as an aqueous emulsion. See, for example, U.S. Pat. No. 4,040,900 (Re. No. 29,960), which describes paper sizing emulsions made from mixtures comprising a substituted cyclic dicarboxylic acid anhydride and polyoxyalkylene alkyl or alkylaryl ether or the corresponding mono- or di-ester.

U.S. Pat. No. 3,968,310 describes half-ester reaction products obtained by reacting maleated alphaolefins with hydrocarbylpolyoxyalkylene alkanols. These half-ester reaction products are useful as hot melt adhesives for paper stocks. However, these compositions suffer the disadvantage of being insoluble in water at neutral or acidic pH and are ineffective in forming aqueous emulsions.

SUMMARY OF THE INVENTION

The present invention provides a novel nonionic emulsifier prepared by the process which comprises heating the reaction product of:
 (a) a hydrocarbyl-substituted succinic anhydride having from 6 to 50 carbon atoms in the substituent; and
 (b) a nonionic water-soluble compound having from 1 to 3 reactive polar groups, wherein said water-soluble compound has sufficient hydrophilic strength to give a balanced oil-in-water emulsifier;
and wherein said reaction product contains a free carboxyl group and a substituted carboxyl group per each reacted anhydride molecule; under conditions sufficient to remove the free carboxyl group.

The invention further provides a stable hydrocarbyl-substituted succinic anhydride/nonionic emulsifier composition comprising 70 to 99.5% of a normally liquid hydrocarbyl-substituted succinic anhydride having from 6 to 50 carbon atoms in the substituent and 0.5 to 30% of the emulsifier described above.

The present invention is also concerned with a method of imparting water repellency to surfaces containing groups reactive to anhydrides which comprises impregnating said surfaces with an aqueous emulsion of the substituted succinic anhydride/nonionic emulsifier composition of the invention.

The present invention is further concerned with a method of sizing paper which comprises intimately dispersing within the wet paper pulp, prior to the ultimate conversion of said pulp into a dry web, an aqueous emulsion of the substituted succinic anhydride/nonionic emulsifier composition of the invention.

Among other factors, the present invention is based on my discovery that certain mono-ester reaction products of substituted succinic anhydride, containing free carboxyl groups, can be heated to form superior emulsifiers which no longer contain the free carboxyl groups. Advantageously, these emulsifiers are unaffected by changes in water hardness, polyvalent cations and pH.

An additional advantage of the present invention is the fact that these emulsifiers can be combined with substituted succinic anhydride to provide stable mixtures which are highly effective in treating various surfaces to impart water repellency. These compositions are particularly useful as superior paper sizing agents.

DETAILED DESCRIPTION OF THE INVENTION

The nonionic emulsifiers of the present invention are derived from certain reaction products of substituted succinic anhydride. These reaction products, which are disclosed in my commonly assigned U.S. patent application, Ser. No. 449,324, filed Dec. 13, 1982, now abandoned and refiled as Ser. No. 814,351, filed Dec. 27, 1985, now U.S. Pat. No. 4,695,401, comprise the reaction product of a hydrocarbyl-substituted succinic anhydride having from 6 to 50 carbon atoms in the substituent and a nonionic water-soluble compound having from 1 to 3 reactive polar groups, wherein said water-soluble compound has sufficient hydrophilic strength to give a balanced oil-in-water emulsifier, and wherein the reaction product contains a free carboxyl group and a substituted carboxyl group per each reacted anhydride molecule. The substituted carboxyl group can have various types of substituents. A preferred type of substituent is an ester linkage. For this reason, I shall refer to these reaction reducts as "mono-esters", although other linkages are also contemplated.

The substituted succinic anhydride useful for preparing the emulsifiers of the present invention is a hydrophobic molecule. Usually it will have one substituent in the 3-position, but it may have substituents in both the 3- and 4-positions. In general, the substituent will be an alkyl, alkenyl or aralkyl group. Other elements may be present in a minor amount, such as a sulfur or ether linkage. The total number of carbon atoms in the substituent is between 6 and 50. A preferred substituent size is between 10 and 30. More preferred is between 12 and 25. A preferred embodiment of the contemplated anhydrides is the alkenyl succinic anhydride made by allowing an olefin to react with maleic anhydride by the well-known "Ene" reaction. Also suitable is the "Diels-Alder" product derived from maleic anhydride and a conjugated diene. For the present purposes, I shall refer to the anhydrides contemplated as "ASA".

The nonionic water-soluble compound suitable for use in preparing the mono-esters can have incorporated a wide variety of polar groups such as amino, amine oxide, hydroxyl, ether, sulfoxide, sulfhydryl, nitro, and the like, to impart water solubility. It must also contain at least one and not more than three groups which will react with the anhydride to produce an ester, amide, or similar linkage, and a free carboxyl group. The number of polar groups must be proportional to the number of reactive groups so that sufficient hydrophilicity is present to balance all the ASA molecules which react. Polyhydric molecules such as sugars are not suitable.

The nonionic water-soluble compound can readily contain small alkyl or alkylene groups in the $C_1$ to $C_4$ range. It can also contain larger alkyl groups as long as the overall molecule has high hydrophilicity. Such molecules would have a hydrophobic-hydrophilic balance outside the normal surfactant/emulsifier range and would be termed "solubilizers".

A particularly useful type of nonionic water-soluble reactant is the polyethylene glycol or polyoxyethylene class of compounds. This class of compounds is well known in the art and is discussed, for example, in U.S. Pat. No. 3,697,438, the disclosure of which is incorporated herein by reference. As described above, these compounds are suitable when they can balance the hydrophobic nature of the ASA. The number of ethylene oxide units can range from about 4 to 50. When two free hydroxyls are present, the number of ethylene oxide units needed will be higher, from about 8 to 100. Lower alkyl or alkylene groups may also be present such as that obtained by capping one end with methyl or ethyl or by incorporating some propylene or butylene glycol. A large detergent range hydrophobic alkyl, acyl or alkylaryl group may only be present if it is overbalanced by a large surplus of polyoxyethylene groups.

Representative examples of the polyethylene glycol class of compounds include polyethylene glycol 1000 (PEG 1000) and methoxy polyethylene glycol 550 (MPG 550). The number which appears after the polyethylene glycol in the above designation represents the degree of polymerization of the polyethylene glycol. More specifically, the number appearing in the designation "polyethylene glycol 1000" indicates that the number of ethylene oxide units in the polymeric compound are such as to yield a total average molecular weight of about 1000. Similarly, methoxy polyethylene glycol 550 has a total average molecular weight of about 550.

A representative example of the class of compounds in which polyethylene glycol is attached to a detergent-range hydrophobe is the alkylphenoxy polyethylene glycol, Igepal CO-850, produced by the GAF Corporation. This material is an ethoxylate of nonylphenol. The number of ethylene oxide units added averages 20. This high an amount of ethylene oxide units overbalances the nonylphenol hydrophobe, placing the compound in the "solubilizer" category, and making it suitable for use in the present invention. In a similar fashion, acyloxy polyethylene glycol may also be employed.

The mono-ester reaction products can be prepared under relatively mild conditions without a catalyst and without needing to handle gaseous, noxious ethylene oxide. The reactants, ASA and the hydrophilic compound, are simply mixed and allowed to react. The hydrophilic reactant should be dry so that anhydride hydrolysis is avoided. A catalyst may be added but it is preferred to conduct the reaction by simple heating. With most hydrophilic reactants, such as the polyethylene glycols, heating for several hours at 80° to 150° C. is satisfactory. For other more or less reactive hydrophilic reactants, the temperature needed may range from room temperature to about 250° C. The ratio of reactants will be close to an equivalent basis, i.e., one anhydride group for each reactive group on the hydrophile. The subsequent emulsifier use may determine when lt is suitable to have some excess of the ASA or of the hydrophilic reagent.

The emulsifiers of the present invention may then be prepared from the mono-ester reaction products by various procedures which remove the carboxyl group while maintaining the oil-in-water emulsifier balance and retaining the property of forming a stable solution in ASA. Contemplated chemical reactions which can effect removal of the carboxyl group include reaction with the double bond in the alkenyl side chain, such as lactonization, unsaturated ketone formation, etc. (see, for example, H. Kwart and K. King, "The Chemistry of Carboxylic Acids and Esters", S. Patai, Editor, Interscience, 1969, page 346); reaction with other carboxyl groups to form anhydride; and reaction with the ester linkage. Oxidation, followed by esterification is also contemplated as long as the emulsifier molecule is not decomposed and no free hydroxyl groups are formed. Free hydroxyl groups will render the emulsifier reactive and therefore unstable when mixed with ASA.

The preferred procedure is to heat without catalysis at a temperature in the range of about 150° to 230° C., preferably about 175° to 215° C. The reaction time will normally vary in the range of about 1 to 500 hours, preferably about 5 to 200 hours. Under these conditions, a high yield of the desired emulsifier can be obtained. Below about 150° C., the conversion rate is too slow without catalysis. Above about 230° C., decomposition may occur.

The process of removing the carboxyl group may be accelerated by using various acidic catalysts described in the literature. Bronsted acids such as $H_2SO_4$, HCl, $BF_3$ complexes, and ion exchange resins could be used to promote lactonization. Lewis acids such as $AlCl_3$ may promote the formation of unsaturated ketones.

The emulsifiers of the present invention are normally prepared stepwise from the hydrocarbyl-substituted succinic anhydride to the mono-derivative (ester, amide, etc.), containing a free carboxyl group, and then to the emulsifier lacking the carboxyl group. However, these steps may be combined into one operation of mixing the reactants and heating. Alternatively, one may start with the succinic acid instead of the anhydride by employing a technique for removing water of esterification.

The novel emulsifiers of the present invention have wide utility in various applications as wetting agents, detergents or emulsifiers. They are water-soluble, giving stable oil-il-water emulsions. The present emulsifiers, as a class, can be either foaming or non-foaming in use. They are similar in effectiveness to the emulsifiers of U.S. Ser. No. 449,324, now abandoned and refiled as Ser. No. 814,351, filed Dec. 27, 1985, now U.S. Pat. No. 4,695,401. The present emulsifiers, however, no longer contain free carboxyl groups. In certain applications, this is advantageous because the carboxyl groups can interact with polyvalent cations to decrease emulsifier effectiveness. In addition, the carboxyl group can ionize, especially at high pH, leading to an increase in the anionic charge on emulsion particles. This could decrease the extent of absorption of the particles in processes such as paper sizing.

The hydrophobic/hydrophilic balance is in the normal emulsifier-detergent range. One way of defining this balance is by the use of the HLB scale (Hydrophile-Lipophile Balance). See P. Becker, . Chapter 18, in "Nonionic Surfactants", M. J. Schick, Editor, Marcel Dekker (1967) On that scale, for my oil-in-water emulsifiers, the HLB should be about 9-16.

In addition to obtaining good emulsifier properties by keeping the HLB below about 16, good solubility at room temperature in the material to be emulsified is desired. When the hydrophilic moiety is polyethylene glycol, for solubility in ASA, the molecular weight of the polyethylene glycol moiety should not be over about 4000.

One particularly attractive use for the novel emulsifiers is in emulsifying ASA in water prior to using the ASA to treat various surfaces to impart water-repellency. Herein are described new ASA/emulsifier mixtures which incorporate this new emulsifier and which are superior to those in the art. These ASA/emulsifier combinations are easy to make at a central location, store and ship to the location where the ASA emulsions will be made.

In general, these novel ASA/emulsifier compositions comprise a mixture of:
 (a) 70 to 99.5% of a normally liquid hydrocarbyl-substituted succinic anhydride containing between 6 and 50 carbon atoms in the substituent; and
 (b) 0.5 to 30% of an emulsifier prepared by the process which comprises heating the reaction product of a hydrocarbyl-substituted succinic anhydride having from 6 to 50 carbon atoms in the substituent and a nonionic water-soluble compound having from 1 to 3 reactive polar groups, wherein said water-soluble compound has sufficient hydrophilic strength to give a balanced oil-in-water emulsifier; and wherein said reaction product contains a free carboxyl group and a substituted carboxyl group per each reacted anhydride molecule; under conditions sufficient to remove the free carboxyl group.

The hydrocarbyl substituent on the succinic anhydride of component (a) will generally be an alkyl, alkenyl or aralkyl group, and preferably alkenyl. A preferred substituent size is between 10 and 30 carbon atoms, more preferably between 12 and 25 carbon atoms.

The two components are miscible and the mixture is liquid at ambient temperatures. It may be prepared by first making the emulsifier composition and dissolving it in the anhydride ("ASA"). In this way, a different ASA may be used for the emulsifier preparation than that used to make the ASA/emulsifier composition. When different ASA's are not needed, a preferred method is to add a very small amount of the emulsifier hydrophilic reactant to the ASA and make the ASA/emulsifier mixture all in one step. Roughly the same time and temperature are required as would be when making the emulsifier separately. The hydrophilic reactant should be dry so that anhydride hydrolysis is avoided. A catalyst may be added but it is preferred to conduct the reaction by heating in the range of 150° to 230° C. as is done when making the emulsifier separately. The amount of hydrophilic compound added is calculated to give the desired mixture of ASA and emulsifier after reaction of the hydrophilic compound with a minor part of the ASA. For example, when 5% of methoxy polyethylene glycol 550 is added to a $C_{18}$ ASA (M.W. 350), 3.2% of the ASA is reacted and the final mixture contains 8.2% emulsifier. Mixtures of hydrophilic reactants may also be employed.

This ASA/emulsifier composition readily emulsifies into water of various hardness and pH with simple mixing in the absence of high shear. Fine droplets are formed and the emulsion is stable until it is used for treating a surface which contains groups reactive to the anhydride. The time between formation and use could range from a few seconds to several hours. Longer times are generally not preferred because the anhydride groups will gradually be hydrolyzed by the water present.

The water used can be relatively pure or can contain the usual impurities in domestic water. It can have a pH above or below 7, generally in the range of 3 to 11. Calcium and magnesium hardness ions may be present.

The amount of ASA suspended in the water can vary widely, from a few parts per million to 10% or more depending on the use and method of application. For wood or fabric treatment, concentrations around 1% may be used, whereas for internal paper sizing, the concentration in the pump slurry is normally below about 100 parts per million. Thereby about 0.1 to 1% of ASA is finally absorbed on the paper.

Surfaces to be treated with the ASA/emulsifier compositions of the invention to gain water repellency will contain integral groups which are reactive to the ASA anhydride group. This normally will involve reaction with groups such as hydroxyl, amino or mercapto. A preferred type of material which may be treated with emulsions of the compositions of the invention contains carbohydrate molecules, such as cellulose or starch, at the surface of the material. These materials contain many hydroxyl groups which can react with the ASA.

As stated above, the ASA/emulsifier compositions of the present invention may be used to impart water repellency to cellulosic materials. The water-repellent compositions described above are preferably applied to the material in aqueous emulsions. The emulsion may be sprayed onto the material or the material may be dipped into the emulsion in order to distribute the derivative evenly throughout the material. The impregnated material is then withdrawn from the solution and air dried. After air drying, the material is then heated, preferably to a temperature in excess of 100° C., to effect a curing of the impregnated agent within the material. It has been found that one may conveniently use a temperature of about 125° C. for a period of 15 to 20 minutes. At lower temperatures, longer periods of time are required to effect the curing process. To be commercially practical, the curing time should be as short as possible and generally less than one hour. At higher temperatures, the heat curing may be accomplished in shorter periods of time. The upper limit of temperature at which the heat curing process may be carried out is limited to the temperatures at which the cellulosic material begins to decompose. Using the composition of the present invention, it is preferred to impregnate the material with from about 0.5 to 3% by weight of the material of the ASA/emulsifier composition.

The ASA/emulsifier compositions of the present invention may additionally be used as paper sizing agents. These novel sizing agents display all of the features and advantages of prior art sizing agents. Moreover, the novel sizing agents of this invention impart to paper sized therewith a particularly good resistance to acidic liquids such as acid inks, citric acid, lactic acid etc. as compared to paper sized with the sizing agents of the prior art. In addition to the properties already mentioned, these sizing agents may also be used in combination with alum as well as with any of the pigments, fillers and other ingredients which may be added to paper. The sizing agents of the present invention may also be used in conjunction with other sizing agents so as to obtain additive sizing effects. A still further advantage is that they do not detract from the strength of the paper and when used with certain adjuncts will, in fact, increase the strength of the finished sheets. Only mild drying or curing conditions are required to develop full sizing value.

The actual use of these sizing agents in the manufacture of paper is subject to a number of variations in technique any of which may be further modified in light of the specific requirements of the practitioner. It is important to emphasize, however, that with all of these procedures, it is most essential to achieve a uniform dispersal of the sizing agent throughout the fiber slurry, in the form of minute droplets which can come in intimate contact with the fiber surface. Uniform dispersal may be obtained by adding the sizing agent to the pulp or by adding a previously formed, fully dispersed emulsion. Chemical dispersing agents may also be added to the fiber slurry.

Another important factor in the effective utilization of the sizing agents of this invention involves their use in conjunction with a material which is either cationic in nature or is, on the other hand, capable of ionizing or dissociating in such a manner as to produce one or more cations or other positively charged moieties. These cationic agents, as they will be hereinafter referred to, have been found useful as a means for aiding in the retention of sizing agents herein as well as for bringing the latter into close proximity to the pulp fibers. Among the materials which may be employed as cationic agents in the sizing process, one may list alum, aluminum chloride, long chain fatty amines, sodium aluminate, substituted polyacrylamide, chromic sulfate, animal glue, cationic thermosetting resins and polyamide polymers. Of particular interest for use as cationic agents are various cationic starch derivatives including primary, secondary, tertiary or quaternary amine starch derivatives and other cationic nitrogen substituted starch derivatives, as well as cationic sulfonium and phosphonium starch derivatives. Such derivatives may be prepared from all types of starches including corn, tapioca, potato, waxy maize, wheat and rice. Moreover, they may be in their original granule form or they may be converted to pregelatinized, cold water soluble products.

Any of the above-noted cationic agents may be added to the stock, i.e., the pulp slurry, either prior to, along with, or after the addition of the sizing agent. However, in order to achieve maximum distribution, it is preferable that the cationic agent be added either subsequent to or in direct combination with the sizing agent. The actual addition to the stock of either the cationic agent or the sizing agent may take place at any point in the paper making process prior to the ultimate conversion of the wet pulp into a dry web or sheet. Thus, for example, these sizing agents may be added to the pulp while the latter is in the headbox, beater, hydropulper or stock chest.

Further improvements in the water resistance of the paper prepared with these novel sizing agents may be obtained by curing the resulting webs, sheets, or molded products. This curing process involves heating the paper at temperatures in the range of from 80° to 150° C. for periods of from 1 to 60 minutes. However, it should again be noted that post curing is not essential to the successful operation of this invention.

The sizing agents of this invention may, of course, be successfully utilized for the sizing of paper prepared from all types of both cellulosic and combinations of cellulosic with non-cellulosic fibers. The cellulosic fibers which may be used include bleached and unbleached sulfate (kraft), bleached and unbleached sulfite, bleached and unbleached soda, neutral sulfite, semichemical chemiground-wood, ground wood, and any combination of these fibers. These designations refer to wood pulp fibers which have been prepared by means of a variety of processes which are used in the pulp and paper industry. In addition, synthetic fibers of the viscose rayon or regenerated cellulose type can also be used.

All types of pigments and fillers may be added to the paper which is to be sized with the novel sizing agents of this invention. Such materials include clay, talc, titanium dioxide, calcium carbonate, calcium sulfate, and diatomaceous earths. Other additives, including alum, as well as other sizing agents, can also be used with these sizing agents.

With respect to proportions, the sizing agents may be employed in amounts ranging from about 0.05 to about 3.0% of the dry weight of the pulp in the finished sheet or web. While amounts in excess of 3% may be used, the benefits of increased sizing properties are usually not economically justified. Within the mentioned range the precise amount of size which is to be used will depend for the most part upon the type of pulp which is being utilized, the specific operating conditions, as well as the particular end use for which the paper is destined. Thus, for example, paper which will require good water resistance or ink holdout will necessitate the use of a higher concentration of sizing agent than paper which does not.

The following examples are provided to illustrate the invention in accordance with the principles of this invention but are not to be construed as limiting the invention in any way except as indicated by the appended claims.

EXAMPLES

EXAMPLE 1

The alkenyl succinic anhydride (ASA) used in this experiment was prepared from maleic anhydride and a mixture of $C_{18}$ straight-chain internal olefins. This ASA, called isooctadecenyl succinic anhydride (7.01 g, 0.02 moles), was mixed with an alkylphenol ethoxylate, Igepal CO-850 (22.06 g, 0.02 moles), which contains an average of about 20 moles of ethylene oxide.

The mixture was heated at 95° C. for 19 hours. This produced a mono-ester derivative of the ASA. Infrared analysis showed the disappearance of anhydride carbonyl peaks at 1785 and 1865 $cm^{-1}$, the presence of ester carbonyl absorption at 1735 $cm^{-1}$, and the presence of carboxyl absorption at 1710 and 3150 $cm^{-1}$.

This mono-ester was further heated at 185° C. to cause loss of the carboxyl groups. Infrared analysis showed the loss of carboxyl absorption with retention of the ester carbonyl. A new carbonyl absorption appeared at 1770 $cm^{-1}$, indicating gamma-lactone. Some anhydride absorption reappeared, apparently from transesterification. By the end of the heating period, 144 hours, this carboxyl appeared to be greater than 90%.

NMR analysis and acid titration agreed with the infrared data.

EXAMPLE 2

The emulsifier product of Example 1 was employed to emulsify ASA in water. The ASA used was a broad range alkenyl succinic anhydride suitable for paper sizing. The alkenyl groups fell in the $C_5$–$C_{20}$ range and were derived from a roughly 50/50 mixture of straight-chain internal olefins and branched-chain propylene oligomer.

A 10% solution of the emulsifier was made in the broad range ASA. One drop (0.026 g) of this mixture was shaken with 25 ml of water for 15 seconds in a stoppered graduate A stable white emulsion was formed.

The 10% solution of emulsifier in ASA was heated at 80° C. for 3 hours, and the emulsion test repeated. A similar stable emulsion was formed. This shows that the ASA/emulsifier mixture is stable to storage.

EXAMPLE 3

The procedure of Example 1 was repeated, except that the starting ASA was the broad range alkenyl succinic anhydride described in Example 2 instead of isooctadecenyl succinic anhydride. The same times and temperatures as in Example 1 were used for making the mono-ester and converting it to the carboxyl-free emulsifier. Practically identical infrared spectra were obtained. This demonstrates that branched-chain ASA is as equally suitable as straight-chain ASA in preparing the emulsifiers of the present invention.

EXAMPLE 4

The emulsifier of Example 3 was dissolved in the broad range alkenyl succinic anhydride described in Example 2. Aqueous emulsions were prepared as in Example 2. As before, very good emulsions were easily made, both when the 10% emulsifier in ASA was fresh and after it was aged by heating at 80° C. for 3 hours.

EXAMPLE 5

The procedure of Example 3 was followed, except that the hydrophilic reactant was methoxy polyethylene glycol 550 (average molecular weight=550). The monoester was formed by heating at 95° C. for 15 hours. On further heating at 185° C., changes similar to Examples 1 and 3 were observed in infrared spectra. After 20 hours, the carboxyl absorption at 3150 $cm^{-1}$ had decreased by about 70% and about 25% of anhydride had reappeared. On further heating, a total of 26 hours at 185° C. plus 17 hours at 210° C., the anhydride peaks disappeared and conversion to the emulsifier product was over 90%.

Following the procedure of Example 4, this emulsifier was shown to be an excellent emulsifier for ASA, both when freshly mixed and after accelerated aging.

EXAMPLE 6

Two experiments were performed on the mono-ester of Example 1 using acid catalysis to reduce the carboxyl content. In one experiment, 3.6% of boron trifluoride was dissolved and complexed with the mono-ester. Some warming occurred. After 40 hours at room temperature, the boron trifluoride was removed by passing over potassium carbonate. Infrared analysis showed that the carboxyl group had largely disappeared. A new peak at 1575 $cm^{-1}$ appeared, probably due to chelated ketone.

In the second experiment, the same procedure was followed except that 0.5% of concentrated sulfuric acid was employed for 3 hours at a little above room temperature. An infrared spectrum showed a similar drop in carboxyl absorption and the appearance of the 1575 $cm^{-1}$ band, but also showed substantial hydroxyl absorption.

These two products were tested for emulsifying power by the procedure of Example 2. Both products formed excellent, stable emulsions when freshly mixed with ASA. When heated for 16 hours at 80° C. to simulate storage, the boron trifluoride product was still a very effective emulsifier, whereas the sulfuric acid product, which contained hydroxyl groups, was a poor emulsifier.

What is claimed is:

1. An emulsifier prepared by the process which comprises heating the reaction product of:
   a. a hydrocarbyl-substituted succinic anhydride having from 12 to 25 carbon atoms in the substituent; and
   b. a nonionic water-soluble compound having from 1 to 3 groups reactive to anhydrides, wherein said water-soluble compound has sufficient hydrophilic strength to give a balanced oil-in-water emulsifier; and wherein said reaction product contains a free carboxyl group and a substituted carboxyl group per each reacted anhydride molecule; under conditions sufficient to remove the free carboxyl group.

2. The emulsifier according to claim 1, wherein the heating is carried out at a temperature in the range of about 150° and 230° C.

3. The emulsifier according to claim 1, wherein the heating is carried out at a reaction time in the range of about 1 to 500 hours.

4. The emulsifier according to claim 1, wherein the hydrocarbyl substituent is selected from the group consisting of alkyl, alkenyl and aralkyl.

5. The emulsifier according to claim 4, wherein the hydrocarbyl substituent is alkenyl.

6. The emulsifier according to claim 1, wherein the water-soluble compound further contains polar groups independently selected from the group consisting of amino, amine oxide, hydroxyl, ether, sulfoxide, sulfhydryl and nitro.

7. The emulsifier according to claim 1, wherein the water-soluble compound is selected from the group consisting of polyethylene glycol, alkoxy polyethylene glycol, alkylphenoxy polyethylene glycol and alyloxy polyethylene glycol.

8. The emulsifier according to claim 1, wherein the hydrophobic/hydrophilic balance is in the range of about 9 to 16 on the HLB scale.

9. A stable hydrocarbyl-substituted succinic anhydride/nonionic emulsifier composition comprising:
   a. 70 to 99.5% of a normally liquid hydrocarbyl-substituted succinic anhydride having from 12 to 25 carbon atoms in the substituent; and
   b. 0.5 to 30% of an emulsifier prepared by the process which comprises heating the reaction product of a hydrocarbyl-substituted succinic anhydride having from 12 to 25 carbon atoms in the substituent and a nonionic water-soluble compound having 1 to 3 groups reactive to anhydrides, wherein said water-soluble compound has sufficient hydrophilic strength to give as balanced oil-in-water emulsifier; and wherein said reaction product contains a free carboxyl group and a substituent carboxyl group per each reacted anhydride molecule; under conditions sufficient to remove the free carboxyl group.

10. The composition according to claim 9, wherein the heating is carried out at a temperature in the range of about 150° to 230° C.

11. The composition according to claim 9, wherein the heating is carried out at a reaction time in the range of about 1 to 500 hours.

12. The composition according to claim 9, wherein the hydrocarbyl substituents of components (a) and (b) are independently selected from the group consisting of alkyl, alkenyl and aralkyl.

13. The composition according to claim 12, wherein the hydrocarbyl substituents of components (a) and (b) are alkenyl.

14. The composition according to claim 9, wherein the water-soluble compound further contains polar groups independently selected from the group consisting of amino, amine oxide, hydroxyl, ether, sulfoxide, sulfhydryl and nitro.

15. The composition according to claim 9, wherein the water-soluble compound is selected from the group consisting of polyethylene glycol, alkoxy polyethylene glycol, alkylphenoxy polyethylene glycol and acyloxy polyethylene glycol.

16. The composition according to claim 9, wherein the emulsifier of component (b) has a hydrophobic/hydrophilic balance in the range of about 9 to 16 on the HLB scale.

17. The composition according to claim 9, wherein the composition is in the form of an aqueous emulsion.

* * * * *